US007578296B2

(12) United States Patent
Miller et al.

(10) Patent No.: US 7,578,296 B2
(45) Date of Patent: Aug. 25, 2009

(54) MALE CHASTITY APPARATUS, METHOD, AND SYSTEM

(75) Inventors: A. Frank Miller, Wellington, UT (US); Doris L. Miller, Wellington, UT (US)

(73) Assignee: A.L. Enterprises, Inc, Price, UT (US)

( * ) Notice: Subject to any disclaimer, the term of this patent is extended or adjusted under 35 U.S.C. 154(b) by 210 days.

(21) Appl. No.: 11/567,040

(22) Filed: Dec. 5, 2006

(65) Prior Publication Data

US 2008/0127986 A1    Jun. 5, 2008

(51) Int. Cl.
  *A61F 5/37* (2006.01)
(52) U.S. Cl. .......................................... 128/883; 600/39
(58) Field of Classification Search ................. 128/883, 128/869; 119/838, 814; 600/38, 39, 41
  See application file for complete search history.

(56) References Cited

U.S. PATENT DOCUMENTS

| 397,106 | A | * | 2/1889 | Bowen ........................ 128/883 |
|---|---|---|---|---|
| 934,240 | A | * | 9/1909 | Tunnessen ................... 128/883 |
| 997,067 | A | | 7/1911 | Lang |
| 1,215,028 | A | | 2/1917 | Jones |
| 4,014,044 | A | | 3/1977 | Figueroa et al. ..................... 2/2 |
| 4,164,217 | A | | 8/1979 | Schrock ....................... 128/138 |
| 4,599,751 | A | | 7/1986 | Bouwhuis ....................... 2/400 |
| 5,163,447 | A | | 11/1992 | Lyons ......................... 128/844 |
| 5,192,271 | A | | 3/1993 | Kalb et al. ................... 604/116 |
| 5,238,009 | A | | 8/1993 | House ......................... 128/883 |
| 5,368,050 | A | | 11/1994 | Donelan ...................... 128/884 |
| 5,485,636 | A | | 1/1996 | Yandell .......................... 2/406 |
| 5,524,638 | A | | 6/1996 | Lyons ......................... 128/844 |
| 5,713,830 | A | | 2/1998 | Tucker et al. .................. 600/38 |
| 5,752,933 | A | | 5/1998 | Morrison ..................... 604/116 |
| 5,845,642 | A | | 12/1998 | Vanmoor ..................... 128/869 |
| 5,899,875 | A | | 5/1999 | Millot et al. ................... 604/20 |
| 6,033,374 | A | | 3/2000 | Miller, Jr. ..................... 602/36 |
| 6,090,088 | A | | 7/2000 | Nichols ....................... 604/347 |
| 6,203,491 | B1 | | 3/2001 | Uribe |
| 6,736,142 | B2 | | 5/2004 | Sanchez Gomez .......... 128/869 |

(Continued)

OTHER PUBLICATIONS

CB-2000- Leather & Lingerie- Lingerie, Male Chastity Devices & Adult Novelties [online], Oct. 31, 2004 [retrieved Oct. 23, 2008]. Retrieved from the Internet <http://web.archive.org/web/20041031003821/http://www.cb-2000.com/cb3000.html>.*

(Continued)

*Primary Examiner*—Patricia Bianco
*Assistant Examiner*—James M Robinson
(74) *Attorney, Agent, or Firm*—Kunzler & McKenzie (57) ABSTRACT

A male chastity system comprises a housing and a partial ring configured for placement behind the scrotum of the user. The partial ring contains a gap. A bridge bridges the gap by attaching to the partial ring at first and second attachment points. The bridge comprises a rear portion and a front portion, and the partial ring and the bridge collectively form a ring. Guide pins extend at least partially through the rear bridge portion, attachment points, front bridge portion, and housing. A locking pin extends through the bridge and housing, a spacer on the locking pin spacing the housing from the ring, and a lock is applied to the locking pin.

16 Claims, 10 Drawing Sheets

U.S. PATENT DOCUMENTS

| | | | |
|---|---|---|---|
| 2002/0033179 A1 | 3/2002 | Burgos | 128/842 |
| 2003/0024536 A1 | 2/2003 | Bagby | 128/883 |
| 2003/0056798 A1 | 3/2003 | Sanchez Gomez | 128/883 |
| 2003/0136415 A1 | 7/2003 | Lanton, Jr. | 128/842 |
| 2004/0094163 A1 | 5/2004 | Benson | 128/844 |
| 2005/0124854 A1* | 6/2005 | Suchy et al. | 600/39 |

OTHER PUBLICATIONS

CB-2000- Leather & Lingerie- Lingerie, Male Chastity Devices & Adult Novelties [online], Oct. 31, 2004 [retrieved Oct. 23, 2008]. Retrieved from the Internet <http://web.archive.org/web/20041031003821/http://www.cb-2000.com/cb3000.html>.*

Chastity Devices CB3000.Sensual Pleasures, URL:http//web.archive.org/web/200604271404/http://www.cb3000.html>.

* cited by examiner

MALE CHASTITY APPARATUS, METHOD, AND SYSTEM

BACKGROUND OF THE INVENTION

1. Field of the Invention

This invention relates to chastity devices, and more particularly to male chastity apparatuses, methods, and systems.

2. Description of the Related Art

Chastity devices have a long and storied history, some forms of them dating back millennia. While female chastity devices are more common, male chastity devices have also been manufactured and used for some time. Generally, a device of this type is installed and locked onto a man's genitals, with the key or other device or method for unlocking it generally being held by the man's sexual partner, ensuring that the man engages in no sexual activity except with the key holder.

Female chastity devices are generally easier to conceive of and manufacture than their male counterparts, since they have the relatively simple goal of preventing penetration and deal with the relatively simple external female anatomy. Male chastity devices, at least effective ones, have proven to be more difficult to create given the external nature of male genitalia. Prior art devices have often proven to be wildly complicated, requiring belts, straps, harnesses, even rigid pants and suspenders. They often require large, unwieldy attachments to the penis and testicles, making them cumbersome, unsightly—even beneath clothing—and uncomfortable for the user. Further complications arise from the need to provide an outlet for urination.

From the foregoing discussion, it should be apparent that a need exists for a male chastity device that is effective, unobtrusive, and comfortable for the user.

SUMMARY OF THE INVENTION

The present invention has been developed in response to the present state of the art, and in particular, in response to the problems and needs in the art that have not yet been fully solved by currently available male chastity devices and systems. Accordingly, the present invention has been developed to provide an apparatus, method, and system for male chastity that overcome many or all shortcomings in the art.

In one aspect of the invention, a male chastity apparatus includes a housing configured to contain the penis of a user and a partial ring configured for placement behind the scrotum. The partial ring contains a gap, and a bridge configured to bridge the gap of the partial ring is provided. The partial ring and the bridge collectively form a ring. A connector disposed between the ring and the housing rigidly attaches the ring to the housing.

In an embodiment of the invention, the ring is approximately cylindrical and its lower portion is relatively thin compared to its upper portion, the ring's thickness gradually changing from its lower to its upper portion. The bridge may include a rear bridge piece and a front bridge piece configured to abut each other. The partial ring comprises first and second mounts, and the rear and front bridge pieces configured engage the first and second mounts.

In a further aspect of the invention, a male chastity apparatus is prepared by a process comprising providing a partial ring and a bridge configured to convert the partial ring to a complete ring. A housing is provided to house the penis of a user, the housing including a first housing half and a second housing half, each housing half having an edge. The first housing half edge has a plurality of protrusions, and the second housing half edge has a plurality of depressions. The edges of the first and second housing halves are placed in abutting engagement and joined, with the edges being disposed approximately in a vertical plane and the protrusions extending into the depressions. In one embodiment, the edges of the first and second housing halves are plastic and joined through sonic welding.

In a further aspect of the invention, a method of facilitating male chastity includes placing a partial ring beneath the penis and behind the scrotum of a user, attaching a bridge to the partial ring to create a complete ring around the penis, placing the penis into a housing, spacing the housing from the ring by a predetermined distance to accommodate the scrotum, connecting the housing to the ring while maintaining the spacing between the housing and the ring, and locking the housing in place.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Discussion of the features and advantages, and similar language, throughout this specification may, but do not necessarily, refer to the same embodiment.

The described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention. These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention will be rendered by reference to specific embodiments illustrated in the appended drawings, which depict only typical embodiments of the invention and are not to be considered limiting of its scope, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
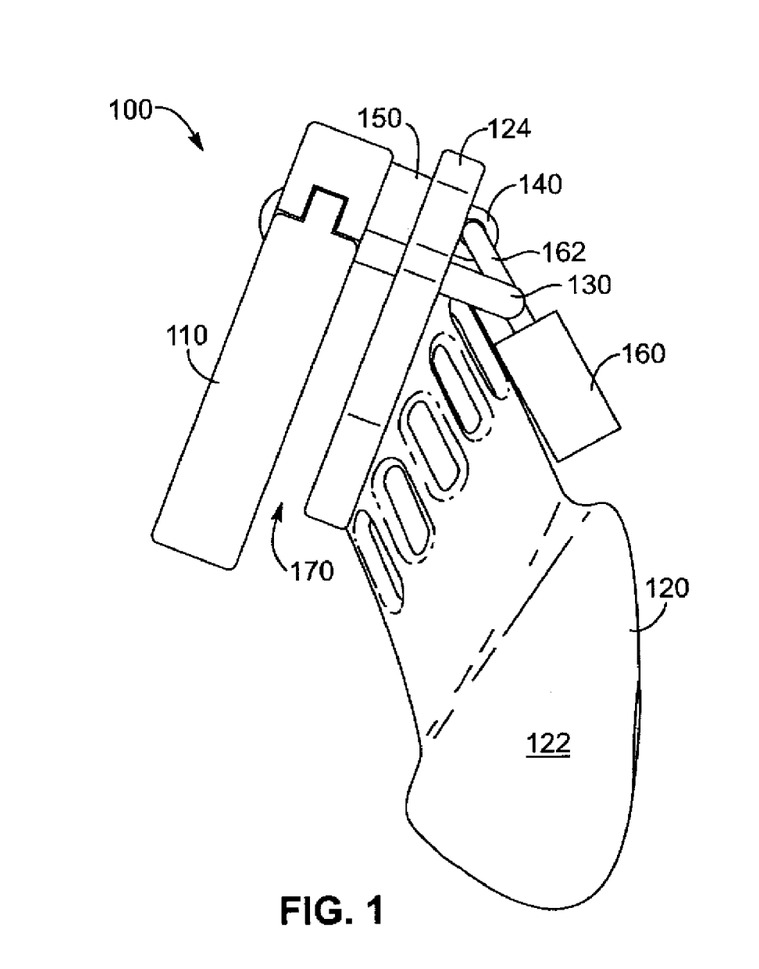
FIG. 1 is a side elevational view of one embodiment of a male chastity apparatus according to the present invention.
Figure 1A:
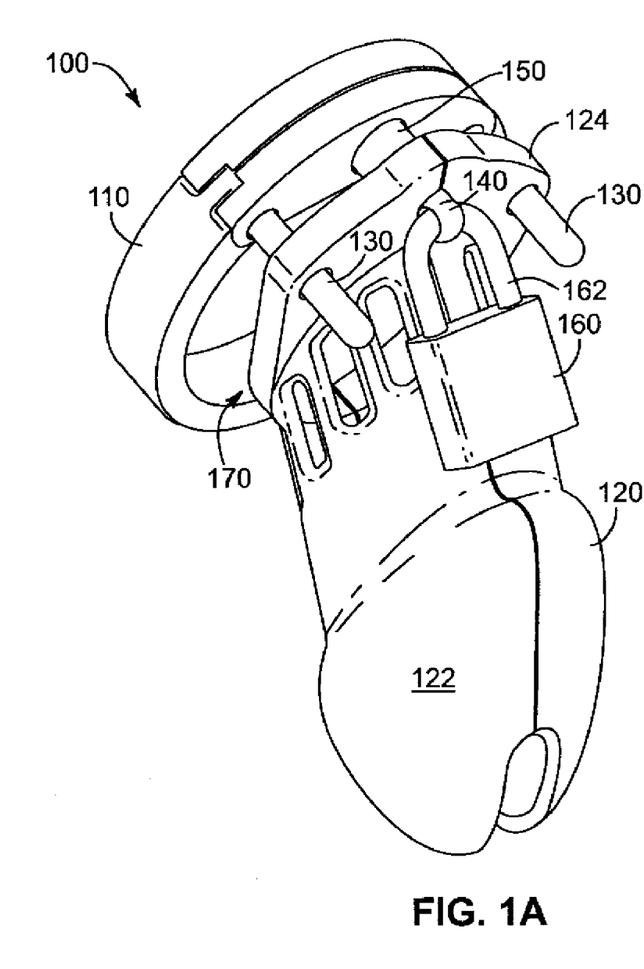
FIG. 1A is a perspective view of the male chastity apparatus of FIG. 1.
Figure 1B:
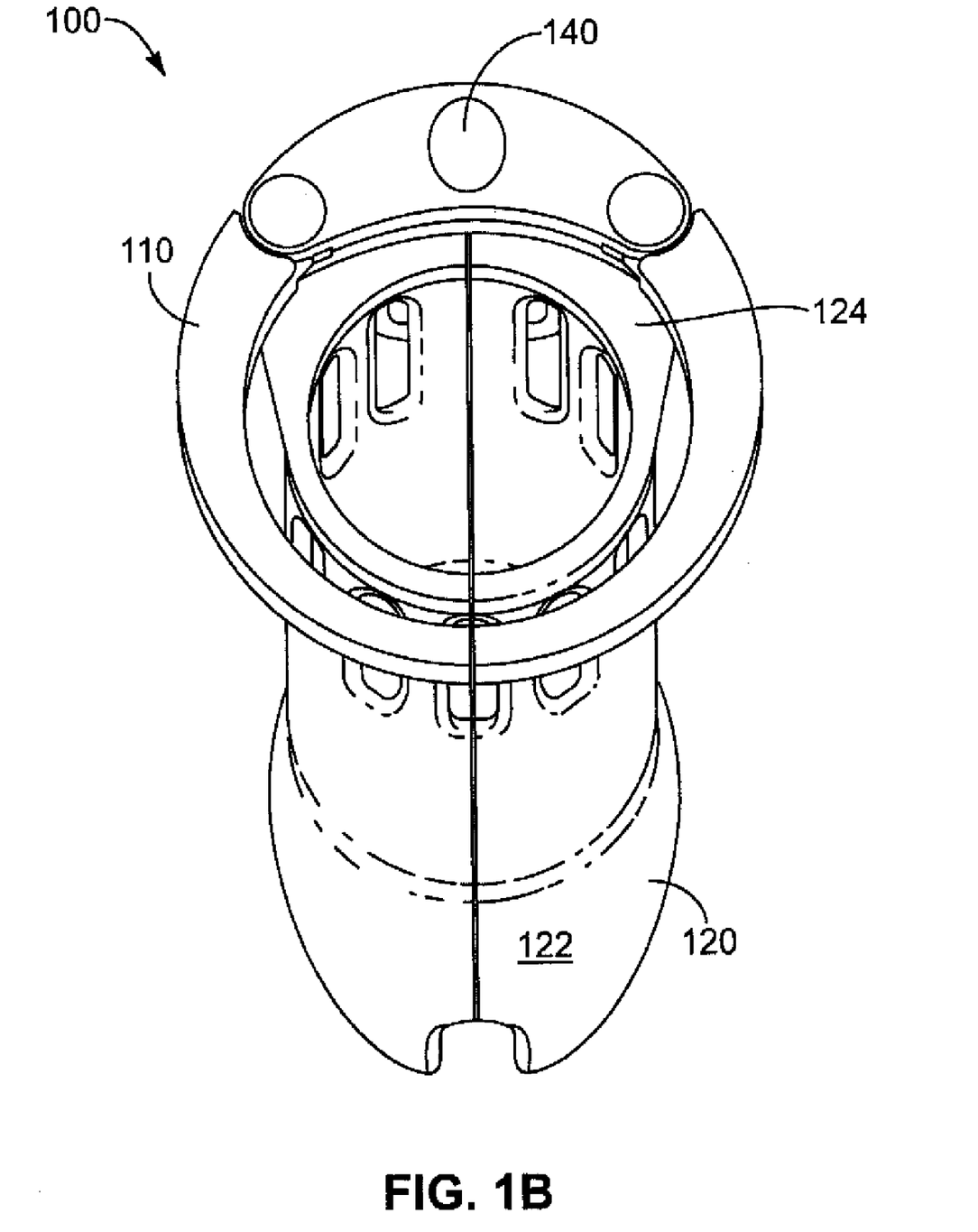
FIG. 1B is a rear elevational view of the male chastity apparatus of FIG. 1.
Figure 1C:
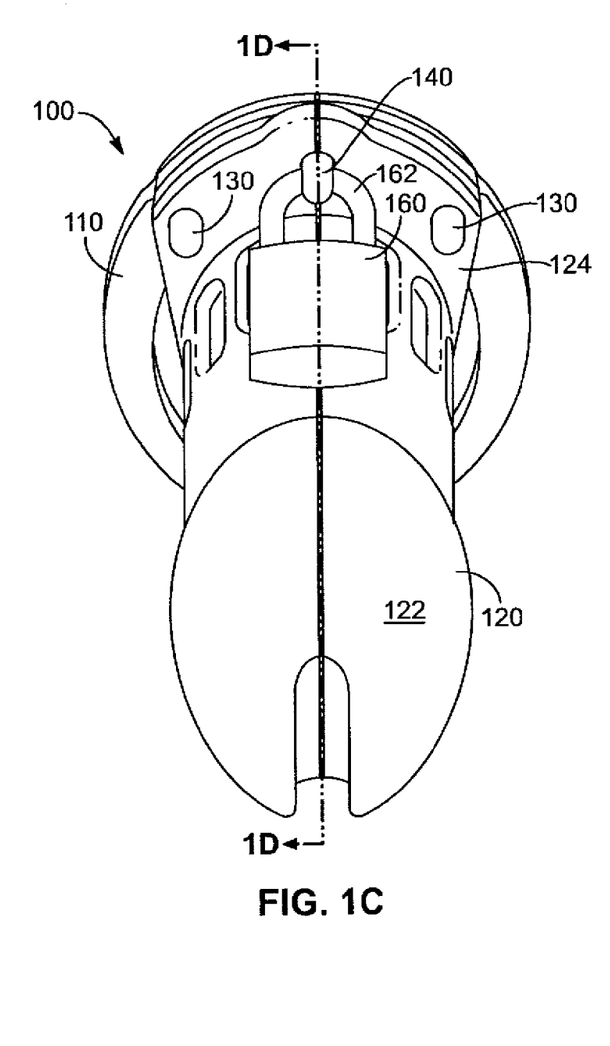
FIG. 1C is a front elevational view of the male chastity apparatus of FIG. 1.
Figure 1D:
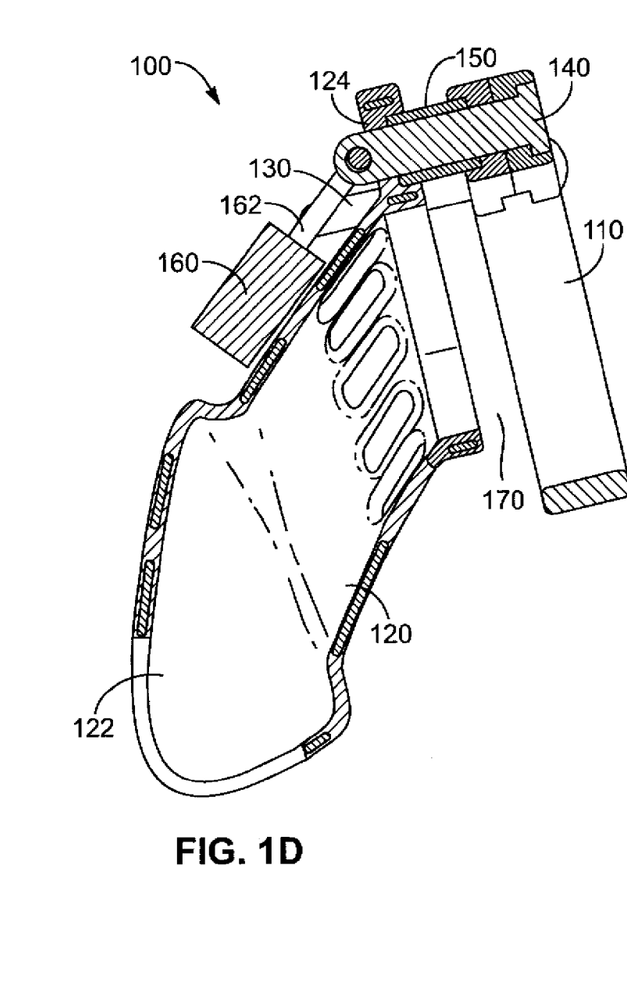
FIG. 1D is a cross-sectional view along line ID-ID of FIG. 1C.

Referring first to FIGS. 1-1D, an embodiment of a male chastity device 100 according to the present invention comprises a ring 110, a housing 120, guide pins 130, a locking pin 140, a spacer 150, and a lock 160.

The ring 110 is configured to be placed around the user's penis behind the scrotum. In one embodiment, the ring 110 is large enough, i.e., of sufficient diameter, to ensure the user's comfort, but small enough to ensure that, once placed, it cannot be removed without unlocking and removing the lock 160 or damaging the device 100. The housing 120, which is configured to house the penis of the user, attaches to the ring 110 with the guide pins 130 and locking pin 140. The spacer 150 provides a space 170 between the ring 110 and housing 120 to accommodate the scrotum, and may be adjusted (through the use of spacers 150 of differing lengths) to be wide enough for comfort but not so wide that the user can withdraw the penis from the housing. The device 100 is designed to allow the testicles of the user to hang below the space 170, between the ring 110 and housing 120.

The housing 120 includes a primary casing 122 and flange 124. The guide pins 130 and locking pin 140 extend through the flange 124. The bail 162 of the lock 160 is attached to the front end of the locking pin 140. In one embodiment, there is little or no play of the housing 120 between the spacer 150 and bail 162, i.e., the spacer 150 and bail 162 hold the housing 120 snugly between them.

The lock 160 can be a standard metal lock, whose combination is known only to or whose key is held by the user's sexual partner. Other locks are also within the scope of the invention, so long as they are sufficient to prevent the locking pin from moving more than a minimal amount relative to the housing 120 and ring 110, thus preventing expansion of the space 170 and preventing the user from removing his penis from the housing 120 without unlocking or damaging the device 100. Disposable plastic locks or loops may be used, preventing sexual activity without cutting the plastic lock or loop. Such an alternative can be useful to prevent embarrassment for users passing through metal detectors in airports or the like.

In use, the device 100 as a whole is generally oriented slightly downwardly, following the natural contours of the body, contributing to the comfort of the user as well as making the device less obtrusive beneath clothing. The housing 120 is shaped and oriented to accommodate the penis of the user while the penis is in a flaccid state.

In one embodiment, most components of the device 100, particularly the housing 120, are manufactured of polycarbonate or similarly rigid plastic material, which can be clear or colored. Some, such as the guide pins 130 and locking pin 140, may be manufactured of acrylic.

The housing 120 prevents physical sexual stimulation of the penis and prevents it from reaching a sexually excited state. Should the user receive visual or other sexually oriented stimuli, the rigidity, shape, and orientation of the housing 120 will create discomfort corresponding to the degree of physical change in the penis, forcing the user to separate himself from the stimuli and/or otherwise take steps to neutralize its effect on him.

Figure 2:
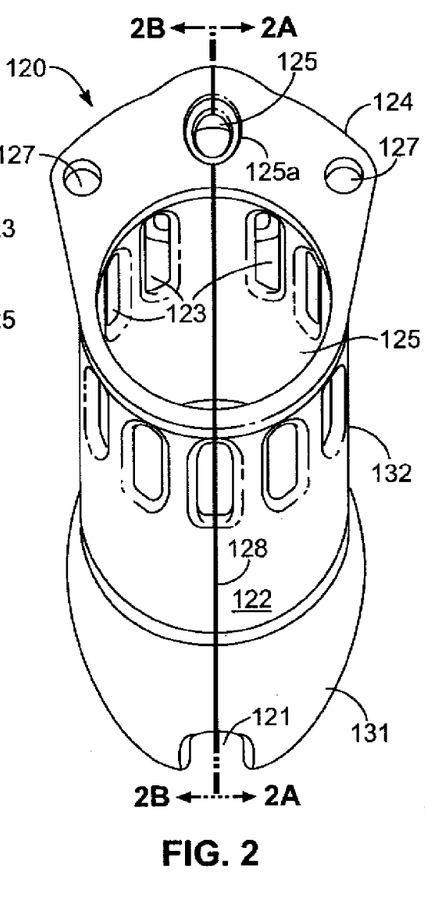
FIG. 2 is a rear elevational view of an embodiment of a housing used in a male chastity apparatus according to the present invention.
Figure 2A:
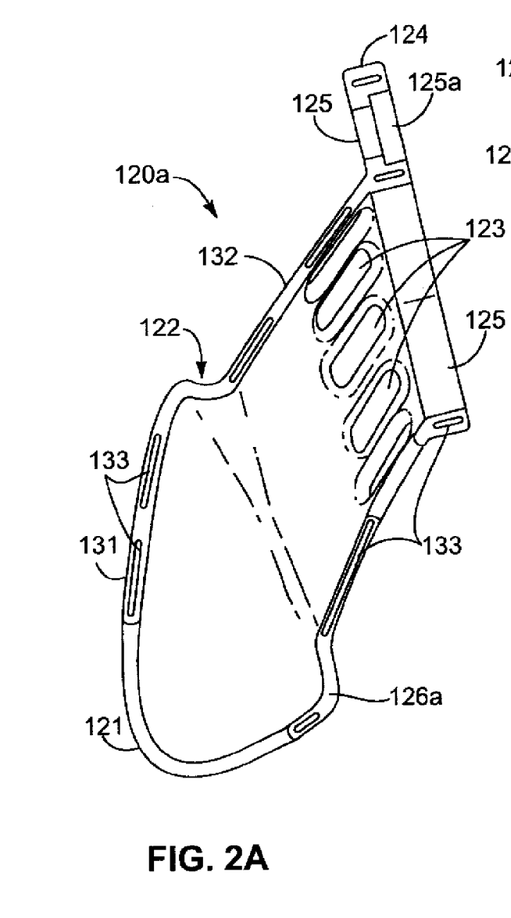
FIG. 2A is a cross-sectional view along line 2A-2A of FIG. 2.
Figure 2B:
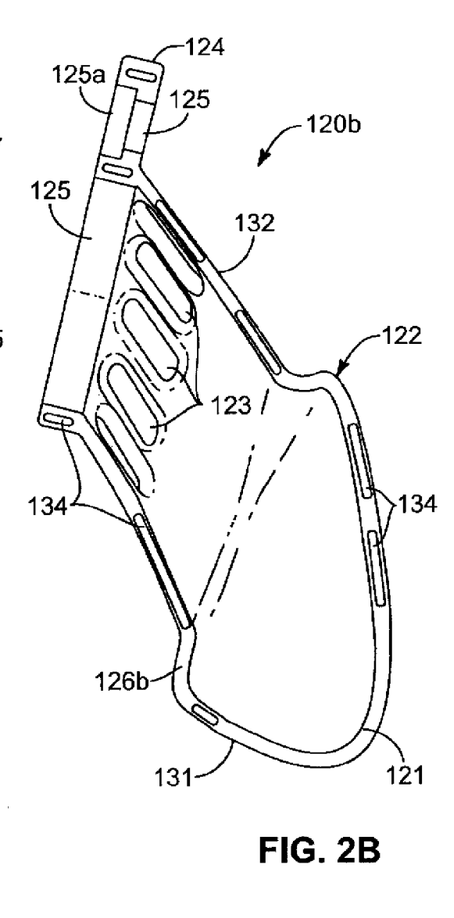
FIG. 2B is a cross-sectional view along line 2B-2B of FIG. 2.

Referring now to FIGS. 2-2B, the housing 120 comprises, as noted above, a primary casing 122 and flange 124. In one embodiment, the casing 122 is shaped approximately like a penis in a flaccid state, including a head 131 and shaft 132. Other shapes are possible, so long as the casing 122 does not allow a large degree of penis expansion or movement.

A urinal passage 121 is disposed at the front end of the head 131 to allow urination while the device 100 is being worn. The urinal passage 121 is relatively small to prohibit manipulation or freedom of movement of the penis.

A series of holes or passages 123 are disposed around the shaft 132 near the rear open end 125 of the housing 120. The passages 123 are elongated and parallel in one embodiment, but other shapes, arrangements, and placements are within the scope of the invention and will be apparent to those skilled in the art in light of this disclosure. The holes 123 allow for cleaning and other hygienic procedures (such as lubrication, to make the device 100 more comfortable to wear) while the device 100 is in use.

The flange 124 of the housing contains a central locking pin passage 125 for accommodation of the locking pin 140, and includes a larger, recessed portion 125a to accommodate the spacer 150. The locking pin passage 125 and recessed portion 125a are oval in cross section in one embodiment to prevent rotation of the locking pin 140 and commensurate movement of the lock 160. The flange 124 also contains guide pin passages 127 for accommodation of the guide pins 130. The placement of the holes 125 and 127, along with the placement of the locking pin 140 and guide pins 130, may be varied from the embodiment shown, as will be apparent to those skilled in the art in light of this disclosure.

The housing 120 comprises two primary components, halves 120a and 120b, shown particularly in FIGS. 2A and 2B, respectively. The housing halves 120a and 120b are mirror images of each other in one embodiment, their edges 126a and 126b being placed in abutting engagement along a vertical plane and forming a vertical joint 128, as shown in FIG. 2, and a cavity configured to receive the penis of the user. In one embodiment, a number of depressions or grooves 133 are formed on the edge 126a of the housing half 120a, and corresponding protrusions 134 are formed on the edge 126b of the housing half 120b, with the protrusions 134 being shaped and placed to fit snugly into the depressions 133 when the edges 126a and 126b are placed together. Such an arrangement helps prevent slippage and lateral movement of the halves 120a and 120b relative to each other.

The halves 120a and 120b may be joined together along the joint 128 through sonic welding, including high-frequency, ultra-sonic, and other types of sonic welding, or other method sufficient to ensure the integrity of the housing 120. The joint 128 may be disposed in a vertical plane to minimize user discomfort arising from imperfections or edges that may be found on the joint 128. Other ways of constructing and forming the housing 120 are within the scope of the invention, as will be apparent to those skilled in the art in light of this disclosure.

Referring now to FIGS. 3-3C and 4-4C, an embodiment of the ring 110 comprises a partial ring 111, which in one embodiment is a partial annulus, i.e., an annulus that does not extend completely in a circle, leaving a gap 112 (FIGS. 4A and 4B) and ends 113. In one embodiment, the ends 113 are smaller extensions of the partial ring 111, and contain passages 114 to accommodate passage of the guide pins 130. The ends 113 form mounts upon which a bridge may be attached to the partial ring 111.

Figure 4A:
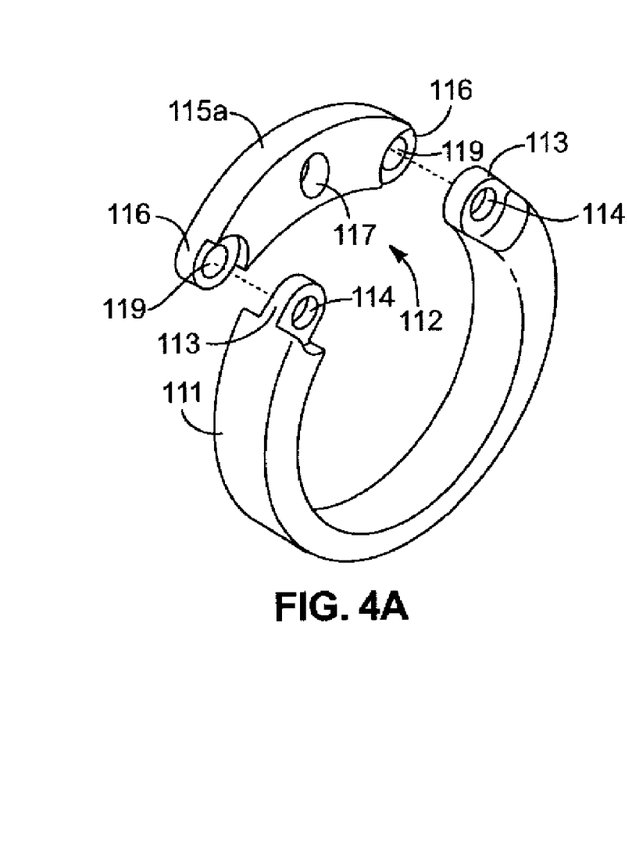
FIG. 4A is an exploded perspective view of the partial ring piece and rear bridge piece of the ring of FIG. 3.
Figure 4B:
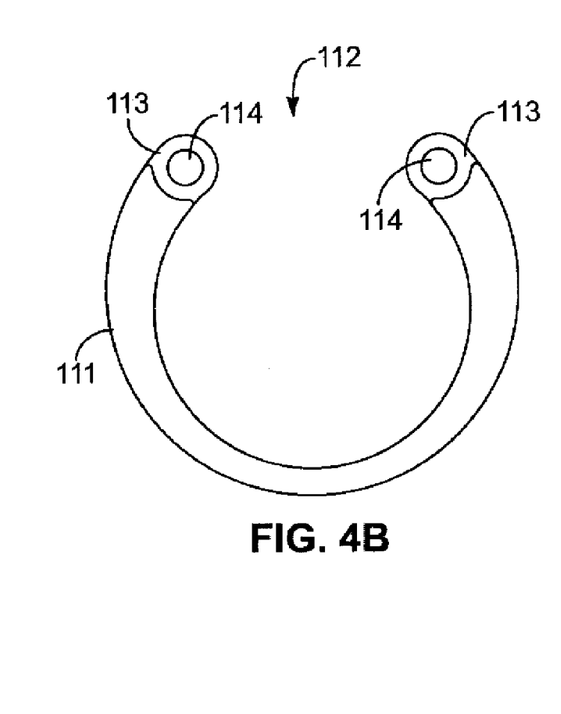
FIG. 4B is a front elevational view of the partial ring piece.
Figure 4C:
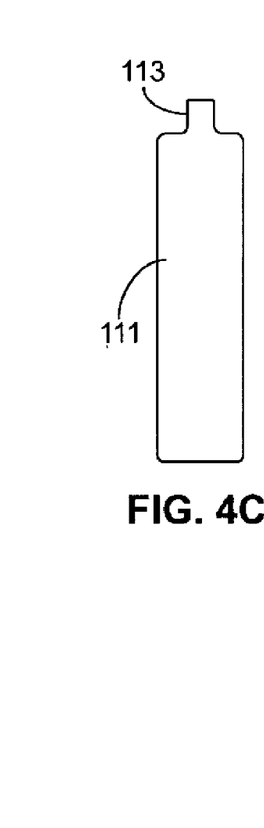
FIG. 4C is a side elevational view of the partial ring piece.

The gap 112 is bridged by a rear bridge piece 115a and front bridge piece 115b, which collectively form a bridge 115 which bridges the gap 112. Each bridge piece 115a and 115b has smaller extending ends 116, which mate with the partial ring ends 113. The ends 116 of the outer bridge piece 115b contain passages which align with the passages 114 when the ends 116 and 113 are mated, forming attachment points and allowing passage of the guide pins 130. The ends 116 and 113 may each be considered attachment points. The ends 116 of the inner bridge piece 115a contain depressions or holes rather than through passages, as further described below, though through passages are also within the scope of the invention. The gap 112 and corresponding bridge 115 may be larger or smaller, longer or shorter, while remaining within the scope of the invention.

In one embodiment, the ends 116 and 113 are shaped such that they fit snugly together and collectively do not substantially change the cross-sectional shape and size of the ring 110 as it transitions from the partial ring 111 to the bridge 115. Differing sizes and shapes may be used and are within the scope of the invention, though they may cause some discomfort to users of the device 100.

A locking pin passage 117, oval-shaped in cross section in one embodiment, is disposed through the rear and front bridge pieces 115a and 115b. Each bridge piece or portion 115a and 15b contains a recess 118a and 118b, respectively (FIG. 3C), the recess 118a accommodating the head of the locking pin 140 and the recess 118b accommodating the spacer 150, each of which fit snugly into their respective recesses in one embodiment. Recessing the head of the locking pin 140 contributes to the comfort of the user.

Figures 3, 3A, 3B, 3C, 4:
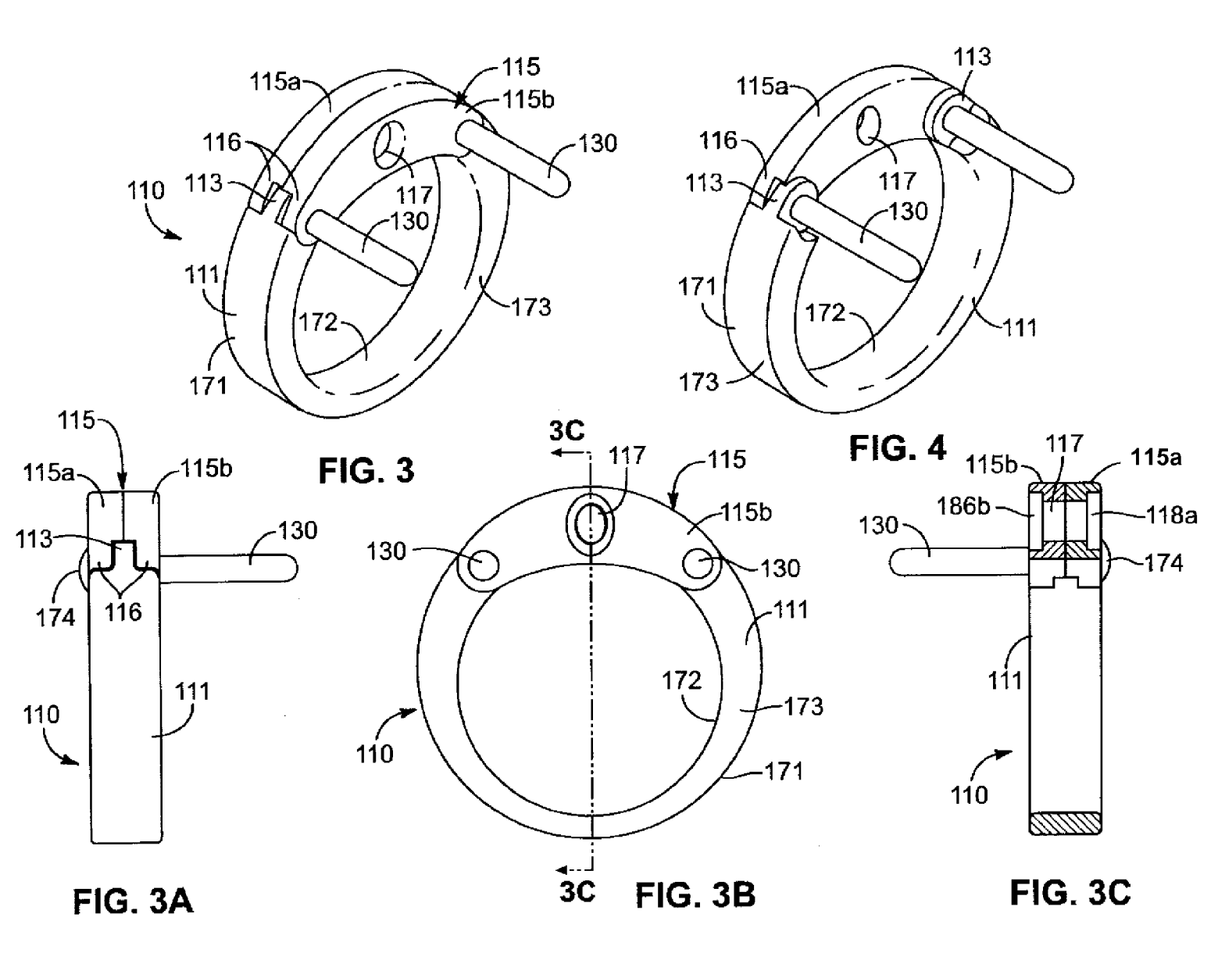
FIG. 3 is a perspective view of an embodiment of a ring and guide pins used in a male chastity apparatus according to the present invention.
FIG. 3A is a side elevational view of the ring and guide pins of FIG. 3.
FIG. 3B is a front elevational view of the ring and guide pins of FIG. 3.
FIG. 3C is a cross-sectional view along line 3C-3C of FIG. 3B.
FIG. 4 is a perspective view of the ring and guide pins of FIG. 3, with the front bridge piece removed.

The ring 110 can be shaped as a toroid (doughnut) or take other shapes while remaining within the scope of the invention, as will be apparent to those skilled in the art in light of this disclosure. When seen from the front or rear (as in FIG. 3B, showing an approximately circular configuration), the ring 110 can be in the shape of a square, diamond, or other shape, though user comfort may be compromised.

As shown, the ring 110 is approximately cylindrical, i.e., circular when seen from the front or rear (FIG. 3B), with an outer wall 171 and inner wall 172 and side walls 173, and approximately rectangular in cross section at any point along the ring. In accordance with the overall shape of the ring 110, the bridge 115 is somewhat curved. Oval, circular, or other cross-sectional shapes are also within the scope of the invention.

The ring 110 may be uniform or varied in cross-sectional size. In the embodiment shown, the ring's cross-sectional size is smaller, i.e., the cylinder is thinner, at the lower portion of the ring 110, with the upper portion being larger in cross section, i.e., the cylinder being thicker. Making the ring 110 thinner at its lower portion helps prevent interference with the user's testicles, contributing to comfort, while the thicker upper portion contributes to strength, particularly important in the embodiment shown since the bridge 115 connects to the partial ring 111 at the upper portion of the ring 110. In one embodiment, the thickness of the ring 110 changes gradually from the lower portion to the upper portion to avoid sharp edges or angles that might prove uncomfortable for the user.

Figure 5:
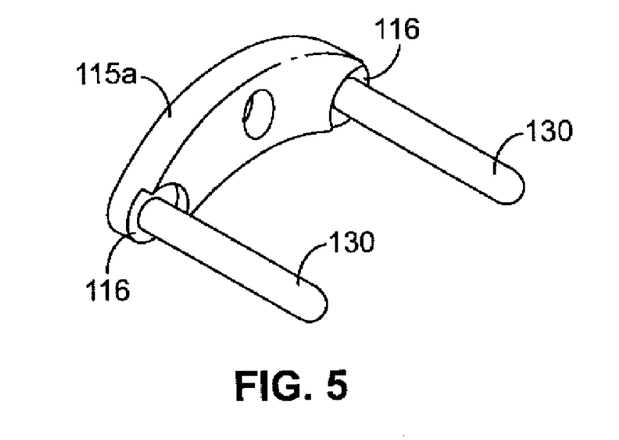
FIG. 5 is a perspective view of an embodiment of a rear bridge piece and guide pins used in a male chastity apparatus according to the present invention.
Figure 5A:
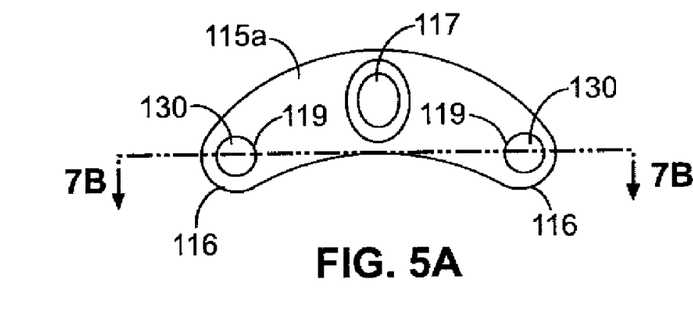
FIG. 5A is a front elevational view of the rear bridge piece and guide pins of FIG. 7.
Figure 5B:
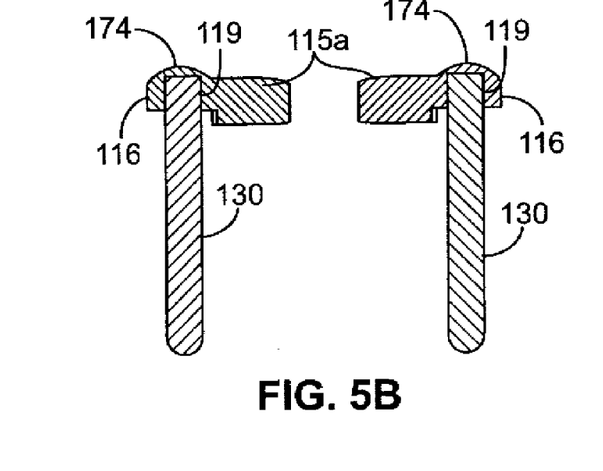
FIG. 5B is a view along line 7B-7B of FIG. 5A.

Referring now to FIGS. 5-5B, the rear bridge piece 115a contains holes 119, which extend partially through the rear bridge piece 115a, allowing the guide pins 130 to be set and, in one embodiment, glued, into the rear bridge piece 115a. Rearwardly protruding bulges 174 (FIGS. 5B, 3A, 3C) provide structural stability to the rear bridge piece 115a in the area of the holes 119.

Figure 6:
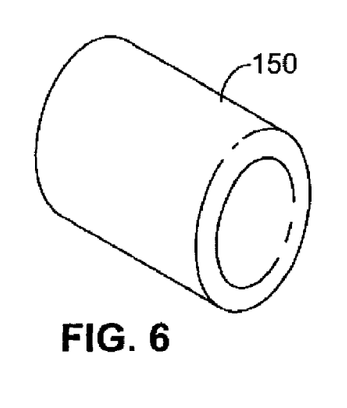
FIG. 6 is a perspective view of an embodiment of a spacer used in a male chastity apparatus according to the present invention.
Figure 6A:
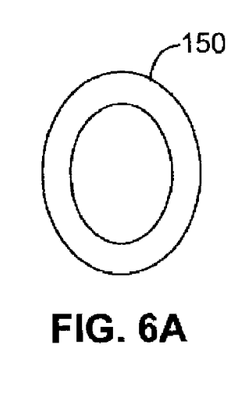
FIG. 6A is a front elevational view of the spacer of FIG. 5.
Figure 6B:
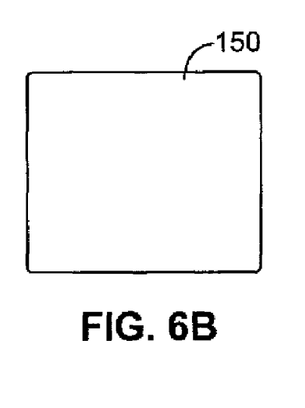
FIG. 6B is a side elevational view of the spacer of FIG. 5.
Figure 7:
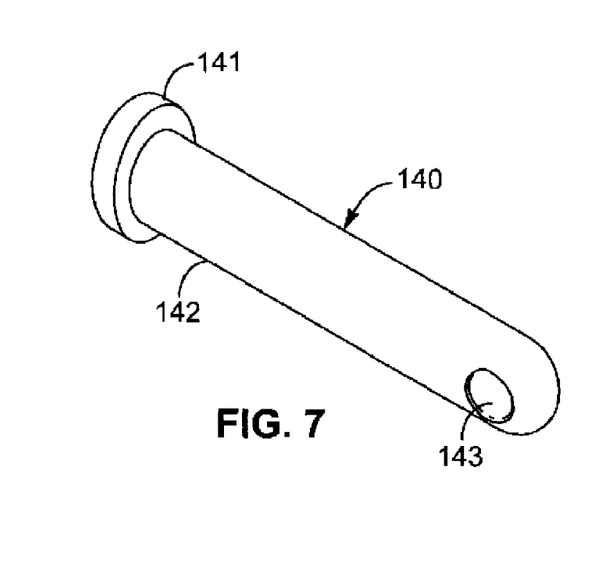
FIG. 7 is a perspective view of an embodiment of a locking pin used in a male chastity apparatus according to the present invention.
Figure 7A:
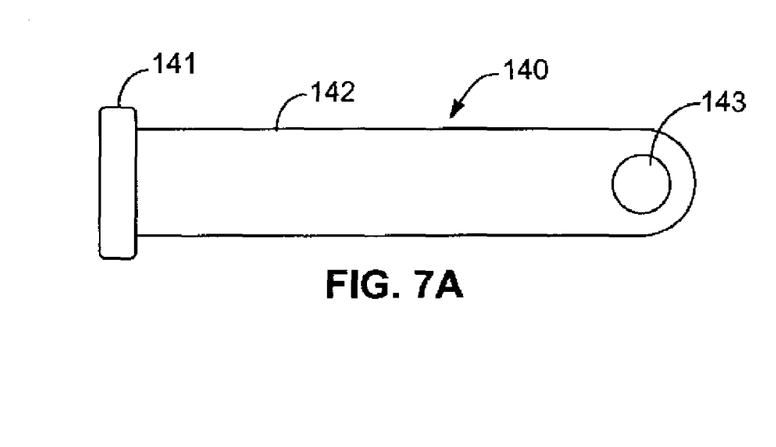
FIG. 7A is a side elevational view of the locking pin of FIG. 6.

Referring now to FIGS. 6-6B, the spacer 150 comprises a cylinder and is approximately oval as seen from the front or rear. Referring to FIGS. 7 and 7A, the locking pin 140 is oval in cross-section in one embodiment, with a head 141 and shaft 142. A passage 143 is disposed in the end of the shaft 142 opposite the head 141 to accommodate the bail 162 of the lock 160.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 8:
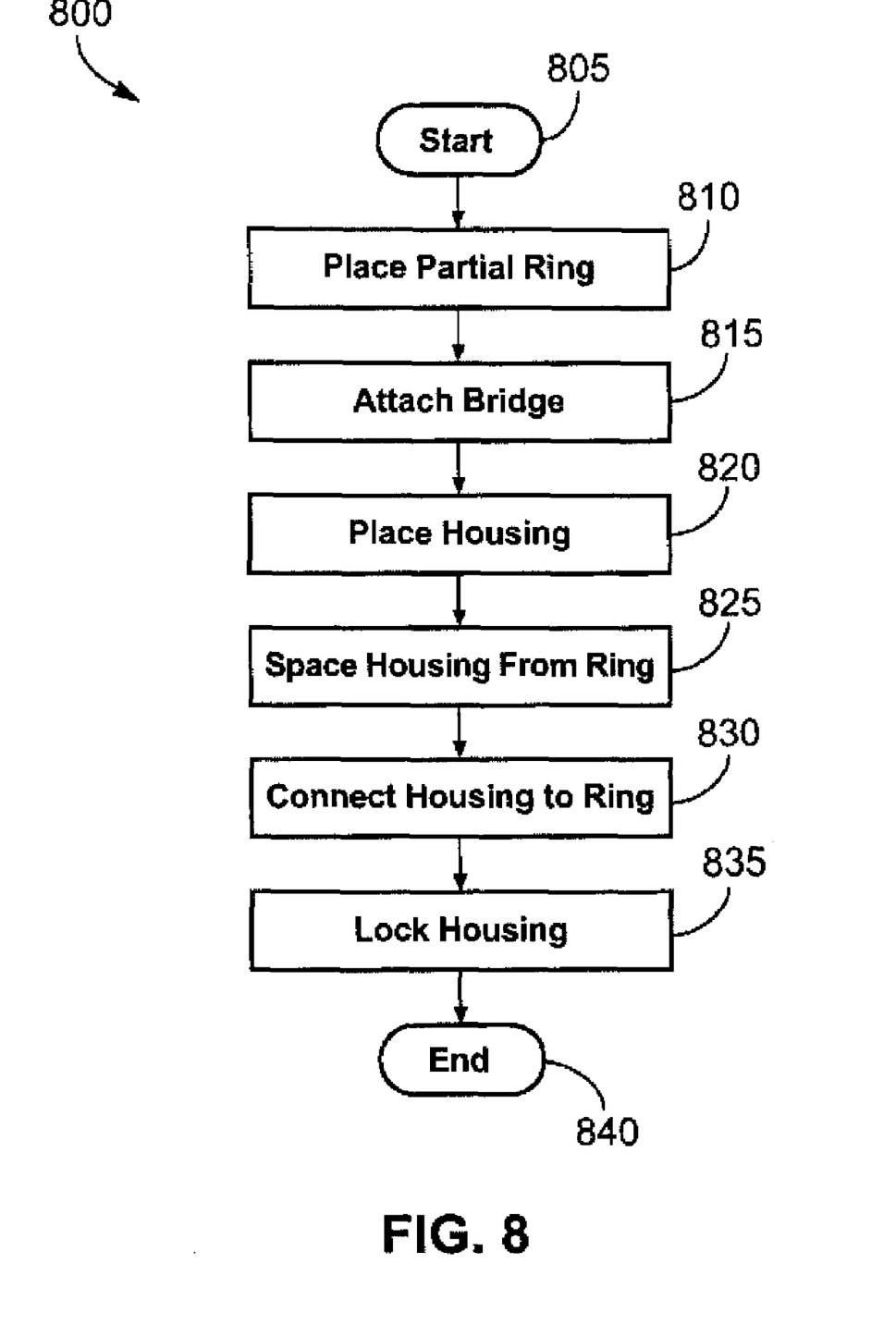
FIG. 8 is a schematic flow chart diagram illustrating an embodiment of a method of ensuring male chastity according to the present invention.

FIG. 8 illustrates an embodiment of a method 800 of ensuring male chastity according to the present invention. The device 100 described above may be used in the method 800.

The method 800 begins in block 805, and in block 810 a partial ring such as the partial ring 111 is placed beneath or on the side of the penis and behind the scrotum of the user. In block 815 a bridge such as the bridge 115 is attached to the partial ring to form a complete ring. If the bridge 115 is used in the method 800, the rear bridge piece 115a may be placed in position relative to the partial ring 111 such that the ends 116 of the rear bridge piece 115a engage with the ends 113 of the partial ring 111. The guide pins 130 may then be inserted through the passages 114 of the partial ring 111 and into the holes 119 of the rear bridge piece 115a. In another embodiment, the guide pins 130 are set into the holes 119 before the rear bridge piece 115a is placed into position on the partial ring 111, such that the piece 115a is placed onto the partial ring 111 by inserting the guide pins 130 through the passages 114.

The front bridge piece 115b may then be slid onto the guide rods 130 until its ends 116 engage with the ends 113 of the partial ring 111 and the rear and front bridge pieces abut each other and form a complete bridge 115. Alternatively, only one of the bridge pieces 115a or 115b may be used to form a bridge, or a single piece of other shape may be used as a bridge. The bridge may also be formed of more than two components. The locking pin 140 may then be inserted through the bridge 115.

In block 820 a housing such as the housing 120 is placed on the user's penis, in block 825 the housing is spaced from a ring such as the ring 110, and in block 830 the housing is connected to the ring. If the device 100 is used in the method 800, the housing 120 may be slid onto the guide rods 130 via the holes 127, with the locking pin 140 extending through the hole 125 and the spacer 150 disposed on the locking pin 140 between the ring 110 and housing flange 124. Different lengths of spacers 150 and locking pins 140 may be used according to the particular user's anatomy, long enough to ensure comfort of the scrotum but short enough to ensure against removal of the penis from the housing casing 122 through the gap 170. Guide pins 130 of commensurate length may be used. Alternatively, or in conjunction, guide pins 130 of excess length may be shortened by cutting.

In block 835 the housing is locked into position, such as by placing the bail 162 of the lock 160 through the passage 143 of the locking pin 140. In one embodiment, the components of the device used in the method 800 are fitted snugly against each other to reduce or eliminate play between components. In block 840 the method 800 ends.

Figure 9:
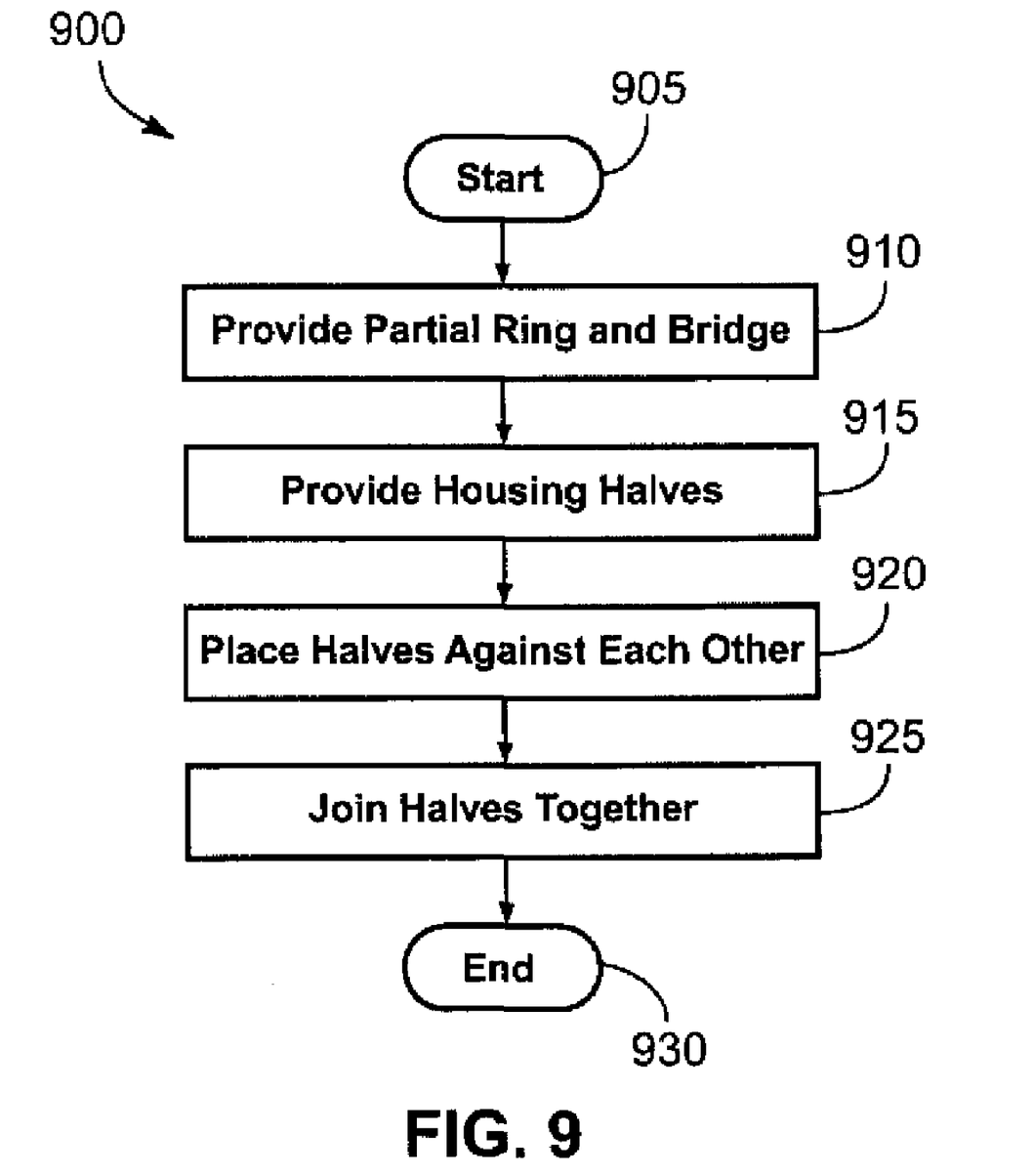
FIG. 9 is a schematic flow chart diagram illustrating an embodiment of a method of preparing a male chastity apparatus according to the present invention.

FIG. 9 illustrates an embodiment of preparing or manufacturing the device 100 according to a method 900 according to the present invention. As shown, the method 900 begins in block 905. In block 910 a partial ring and bridge such as the partial ring 111 and bridge 115 are provided as described above. In block 915 the housing halves 120a and 120b are provided, and in block 920 the housing halves 120a and 120b are placed against each other in abutting engagement along an approximately vertical plane and forming the vertical joint 128, as shown in FIG. 2. In one embodiment, the depressions or grooves 133 on the edge 126a of the housing half 120a and corresponding protrusions 134 on the edge 126b of the housing half 120b are placed together.

In block 925 the halves 120a and 120b are joined together along the joint 128 such as through sonic welding or through other method sufficient to ensure the integrity of the housing 120. The method 900 ends in block 930.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A male chastity apparatus comprising:
   a housing configured to contain the penis of a user;
   a partial ring configured for placement behind the scrotum of the user, the partial ring containing a gap;
   a separate removable bridge configured to bridge the gap of the partial ring, the partial ring and the bridge collectively forming an approximately cylindrical complete ring when the removable bridge is engaged with the partial ring, wherein the removable bridge and the partial ring comprise separate components of the complete ring the complete ring comprising an upper portion that is thicker than a lower portion, the complete ring gradually changing thickness between the lower portion and the upper portion;
   a connector disposed between the complete ring and the housing, the connector rigidly attaching the ring to the housing.

2. The apparatus of claim 1, wherein the separate removable bridge comprises a rear bridge piece and a front bridge piece configured to abut each other, and the partial ring comprises first and second mounts, the rear and front bridge pieces configured to engage the first and second mounts.

3. The apparatus of claim 2, wherein the connector comprises first and second guide pins, the first guide pin being inserted into the rear bridge piece and passing through the first mount, the front bridge piece, and the housing, and the second guide pin being inserted into the rear bridge piece and passing through the second mount, the front bridge piece, and the housing.

4. The apparatus of claim 1, wherein the connector comprises a locking pin configured to pass through the bridge and the housing, with a front portion disposed on the front side of the housing, the locking pin further configured to receive a lock on the front portion, the apparatus further comprising a spacer disposed on the locking pin between the separate removable bridge and the housing.

5. The apparatus of claim 4, wherein the locking pin comprises a head and a shaft, at least one of the head and the shaft having an oval-shaped cross-section, and wherein the locking pin head is recessed into a rear bridge piece, and wherein the spacer is recessed into the bridge and the housing.

6. The apparatus of claim 1, wherein the housing comprises a first primary housing component and a second primary housing component, the first and second components abutting each other along an approximately vertical plane, the first and second components together forming a cavity configured to receive the penis of the user.

7. The apparatus of claim 6, further comprising a plurality of protrusions disposed on the first housing component and a plurality of depressions disposed on the second housing component, the protrusions engaging with the depressions as the first and second housing components abut each other.

8. The apparatus of claim 1, wherein the connector comprises a shaft disposed through the housing and at least partially through the complete ring.

9. The apparatus of claim 1, wherein the housing comprises an approximately penis-shaped casing, the casing comprising a rear end and a front end, and further comprising a plurality of holes disposed approximately uniformly around the casing near the rear end.

10. A male chastity system, the system comprising:
- a housing comprising a casing configured to contain the penis of a user and a flange attached to the casing;
- a partial ring configured for placement behind the scrotum of the user, the partial ring containing a gap;
- a separate removable bridge configured to bridge the gap of the partial ring by attaching to the partial ring at first and second attachment points, the separate removable bridge comprising a rear bridge piece and a separate front, the partial ring, the rear bridge piece and the separate front bridge piece collectively forming a complete ring;
- a first guide pin attached to the rear bridge piece and extending through the first attachment point, through the front bridge piece, and through the flange;
- a second guide pin attached to the rear bridge piece and extending through the second attachment point, through the front bridge piece, and through the flange;
- a locking pin disposed through the rear bridge piece and the front bridge piece of the separate removable piece and through the flange, a front portion of the locking pin disposed on the front side of the housing;
- a spacer disposed on the locking pin between the separate removable bridge and the flange;
- a lock disposed on the front portion of the locking pin.

11. The system of claim 10, wherein the ring is approximately cylindrical.

12. The system of claim 11, wherein the ring is relatively thin opposite the separate removable bridge and relatively thick at the separate removable bridge.

13. The system of claim 10, wherein at least a portion of the locking pin is oval in cross section.

14. A method of facilitating male chastity, the method comprising:
- placing a partial ring beneath the penis and behind the scrotum of a user, the partial ring containing a gap;
- attaching a separate removable bridge to bridge the gap of the partial ring, the partial ring and the bridge collectively forming an approximately cylindrical complete ring around the user's scrotum when the removable bridge is engaged with the partial ring, the complete ring comprising an upper portion that is thicker than a lower portion, the complete ring gradually changing thickness between the lower portion and the upper portion;
- placing the penis into a housing;
- spacing the housing from the ring by a predetermined distance to accommodate the scrotum;
- connecting the housing to the ring while maintaining the spacing between the housing and the ring;
- locking the housing in place.

15. The method of claim 14, wherein the separate removable bridge comprises a first end and a second end, and wherein attaching the separate removable bridge to the partial ring comprises attaching the first end to the partial ring at a first attachment point and the second end to the partial ring at a second attachment point.

16. The method of claim 14, wherein the separate removable bridge comprises first and second bridge pieces, and wherein attaching the separate removable bridge to the partial ring comprises attaching the first bridge piece to the partial ring and attaching the second bridge piece to the partial ring.

* * * * *